United States Patent
Tang et al.

(10) Patent No.: US 11,306,076 B2
(45) Date of Patent: Apr. 19, 2022

(54) SILIBININ LIPOIC ACID ESTER WITH HEPATOPROTECTIVE ACTIVITY AND A METHOD OF PREPARING THE SAME

(71) Applicants: Yonghong Tang, Xi'an (CN); Huafeng Qi, Xi'an (CN); Peiyu Zhou, Xi'an (CN); Xingke Ju, Xi'an (CN); Chengyuan Liang, Xi'an (CN); Yuzhi Liu, Xi'an (CN); Bin Tian, Xi'an (CN); Lei Tian, Xi'an (CN); Gennian Mao, Xi'an (CN); Limei Wang, Xi'an (CN); Yuanyuan He, Xi'an (CN); Yongbo Wang, Xi'an (CN); Jingwen Xu, Xi'an (CN); Dan Yang, Xi'an (CN); Liang Qi, Xi'an (CN); Wenbo Yao, Xi'an (CN); Qianqian Zhao, Xi'an (CN); Han Li, Xi'an (CN)

(72) Inventors: Yonghong Tang, Xi'an (CN); Huafeng Qi, Xi'an (CN); Peiyu Zhou, Xi'an (CN); Xingke Ju, Xi'an (CN); Chengyuan Liang, Xi'an (CN); Yuzhi Liu, Xi'an (CN); Bin Tian, Xi'an (CN); Lei Tian, Xi'an (CN); Gennian Mao, Xi'an (CN); Limei Wang, Xi'an (CN); Yuanyuan He, Xi'an (CN); Yongbo Wang, Xi'an (CN); Jingwen Xu, Xi'an (CN); Dan Yang, Xi'an (CN); Liang Qi, Xi'an (CN); Wenbo Yao, Xi'an (CN); Qianqian Zhao, Xi'an (CN); Han Li, Xi'an (CN)

(73) Assignee: XI'AN TAIKOMED PHARMACEUTICAL TECHNOLOGY CO., LTD., Xi'an (CN)

(*) Notice: Subject to any disclaimer, the term of this patent is extended or adjusted under 35 U.S.C. 154(b) by 0 days.

(21) Appl. No.: 16/871,354

(22) Filed: May 11, 2020

(65) Prior Publication Data
US 2021/0347767 A1 Nov. 11, 2021

(51) Int. Cl.
*C07D 409/14* (2006.01)
*B01J 27/24* (2006.01)

(52) U.S. Cl.
CPC ............ *C07D 409/14* (2013.01); *B01J 27/24* (2013.01)

(58) Field of Classification Search
CPC .............................. C07D 409/14; B01J 27/24
USPC .......................................................... 549/39
See application file for complete search history.

(56) References Cited

U.S. PATENT DOCUMENTS

2018/0208584 A1* 7/2018 Mansour .............. C07D 215/44

OTHER PUBLICATIONS

Koufaki et al Multifunctional Lipoic acid Conjugates (Year: 2009).*
Silibinin—a promising treatment for cancer. Catherine Wing Ying Cheung et al (Abstract) (Year: 2010).*

* cited by examiner

*Primary Examiner* — Timothy R Rozof

(57) ABSTRACT

A compound having the formula (I):

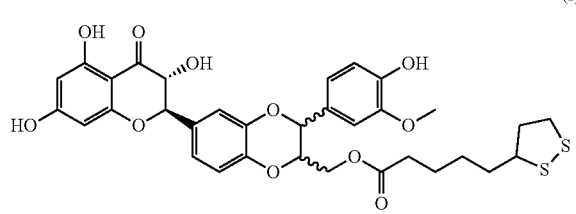

is disclosed. A method of preparing the compound of formula (I) is also disclosed.

15 Claims, 1 Drawing Sheet

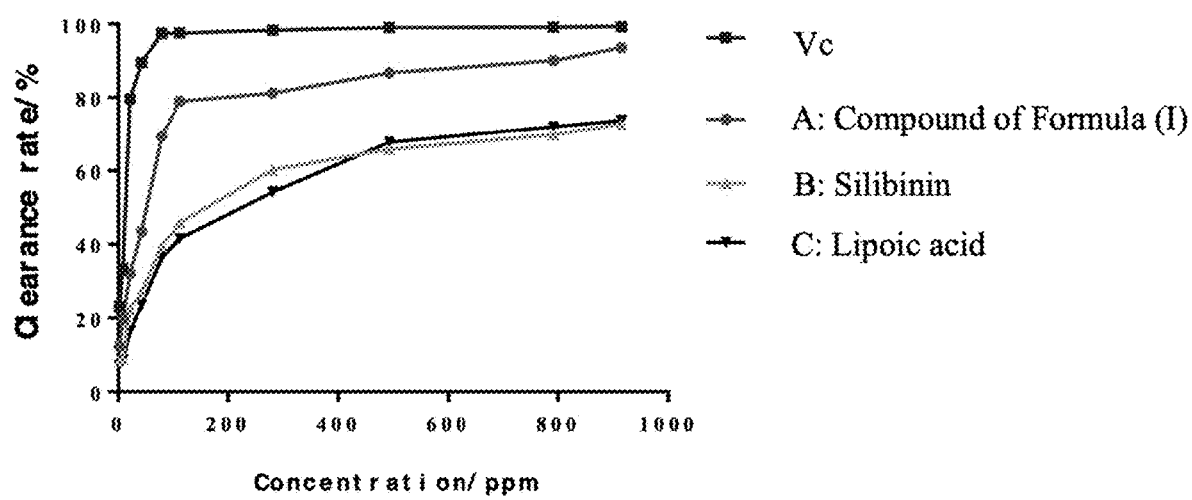

SILIBININ LIPOIC ACID ESTER WITH HEPATOPROTECTIVE ACTIVITY AND A METHOD OF PREPARING THE SAME

FIELD OF THE INVENTION

The present invention relates to the field of medical chemistry, specifically, a silibinin lipoic acid ester, a method of preparing the same, and the application therefor.

BACKGROUND OF THE INVENTION

Liver injury can be caused by many factors, such as alcohol, drugs, and viruses. In modern society, due to excessive mental stress, drinking, smoking and environmental pollution and other reasons, people are faced with a variety of liver diseases, such as spurious cirrhosis, fatty liver, toxic liver disease and acute and chronic viral hepatitis.

Researchers have explored the mechanism of liver injury in many ways. Hepatoprotective drugs, such as membrane protectants, anti-lipid peroxidants, and anti-immune reagents, have been developed, but the efficacy is still unsatisfactory, and its potential toxic and side effects have limited clinical application. Therefore, there is a need to develop new and effective hepatoprotective drugs.

SUMMARY OF THE INVENTION

In one embodiment, the present invention provides a compound having the following formula (I):

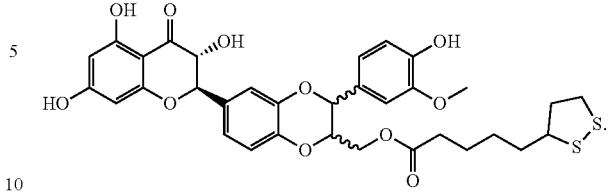

In another embodiment, the present invention provides a method of preparing the compound of formula (I). The method includes: reacting a compound of formula (II) with a compound of formula (III) to obtain the compound of formula (I):

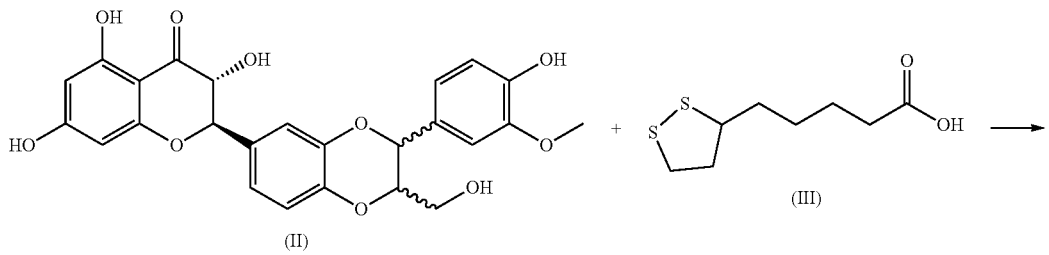

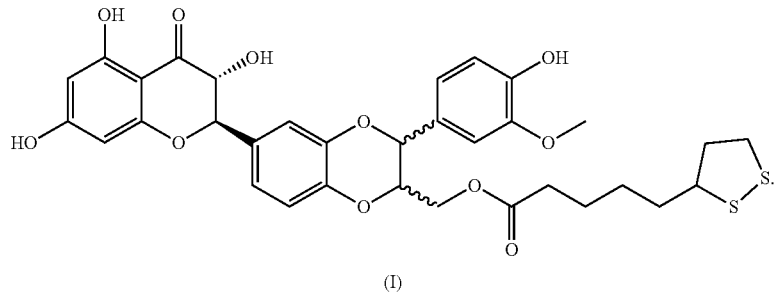

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalyst under nitrogen atmosphere to obtain a reaction mixture; heating the reaction mixture at 50-85° C. for 1-4 hours; concentrating the reaction mixture under reduced pressured to give a crude product; and purifying the crude product on a silica gel column with petroleum ether and ethyl acetate as an eluent to obtain the compound of formula (I).

In another embodiment, the organic solvent is toluene, ethyl acetate, or acetonitrile.

In another embodiment, the catalyst is EDC.

In another embodiment, the molar ratio of the compound of formula (II) and the compound of formula (III) is 1:1.1.

In another embodiment, the reaction mixture is heated at 75° C.

In another embodiment, the reaction mixture is heated for 4 hours.

In another embodiment, the eluent is ethyl acetate:petroleum ether=3:10.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 25-50° C. for 5-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][$BF_4$]).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 25° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the scavenging activity of the compound of formula (I) and control solutions at different concentrations.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Silybin (also known as silibinin) is the extract of the milk thistle seeds, and is a mixture of two diastereomers, silybin A and silybin B.

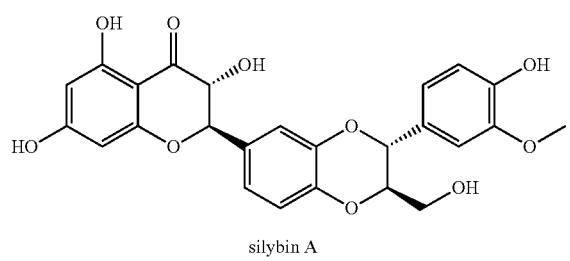

silybin A

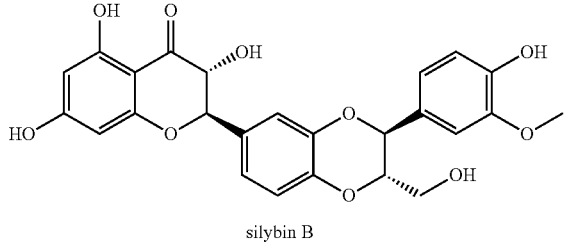

silybin B

In the present application, the mixture of two diastereomers, silybin A and silybin B, is used, and the mixture is shown as the compound of formula (II).

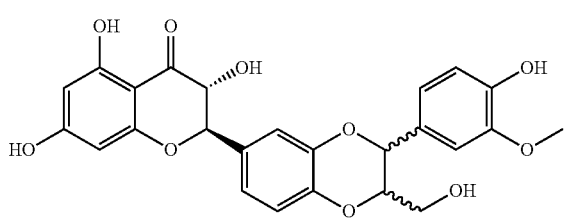

(II)

Lipoic acid (compound of formula (III)) is a coenzyme found in mitochondria, similar to vitamins, which can eliminate free radicals that accelerate aging and disease. It has the characteristics of both fat-soluble and water-soluble, can reach any cell part of the whole body without hindrance, and provides comprehensive efficacy of the human body. It is called universal antioxidant. At the same time, lipoic acid has therapeutic effect on a variety of diseases, and can be used to treat acute and chronic hepatitis, liver cirrhosis, hepatic coma, fatty liver, diabetes and so on.

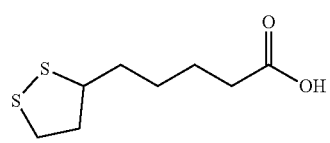

(III)

In the present invention, lipoic acid reacts with silibinin to obtain a silibinin lipoic acid ester. The silibinin lipoic acid ester has excellent hepatoprotective activity and antioxidant activity, and has high medical research and application value a hepatoprotective products.

Example 1

Preparation of (3-(4-hydroxy-3-methoxyphenyl)-6-((2R,3R)-3,5,7-trihydroxy-4-oxochroman-2-yl)-2,3-dihydrobenzo[b][1,4]dioxin-2-yl)methyl 5-(1,2-dithiolan-3-yl)pentanoate (Compound of Formula (I))

In a 250 mL three-necked flask, 241.0 mg (0.50 mmol) of silibinin and 95.8 mg (0.50 mmol) EDC (1-ethyl-3-(3-dimethylaminopropyl)carbodiimide) were dissolved in 90 mL of acetonitrile under nitrogen atmosphere. 113.3 mg (0.55 mmol) of lipoic acid was dissolved in 30 mL of acetonitrile, and slowly added dropwise to the reaction mixture by a separatory funnel. After the completion of the dropwise addition, the temperature was raised to 75° C., and the reaction was carried out for 4 hours. Thin layer chromatography was used to track the reaction to completion, heating was stopped, and the protective device was removed. The concentrated solution was washed with water, extracted with ethyl acetate, dried and concentrated, and a crude product was obtained. The crude product was purified by silica gel column chromatography with petroleum ether:ethyl acetate=3:10 as eluent, and the eluent was concentrated under reduced pressure and dried to obtain 246.6 mg of the titled compound, a yield of 73.61%.

$^1$H-NMR (400 MHz, DMSO-$d_6$) δ (ppm): 7.05 (1H, s), 6.99 (1H, s), 6.82-6.76 (4H, m), 6.23 (1H, s), 5.85 (1H, s), 5.60-5.51 (3H, m), 5.38 (3H, s), 5.21 (1H, t), 4.43 (2H, d), 3.87 (3H, s), 2.82 (1H, d), 2.55 (3H, t), 2.35 (2H, t), 1.78-1.68 (4H, m), 1.57 (2H, t), 1.28 (2H, t); $^{13}$C-NMR (400 MHz, DMSO-$d_6$) δ (ppm): 197.9, 174.1, 165.9, 164.8, 148.2, 143.7, 128.3, 121.7, 119.2, 116.7, 111.8, 110.1, 96.1, 88.4, 80.7, 72.9, 64.5, 57.2, 39.3, 37.4, 33.6, 27.0.

Example 2

Preparation of the Compound of Formula (I)

In a 250 mL three-necked flask, 241.0 mg (0.50 mmol) of silibinin and 95.8 mg (0.50 mmol) EDC were dissolved in 90 mL of toluene under nitrogen atmosphere. 113.3 mg (0.55 mmol) of lipoic acid was dissolved in 30 mL of toluene, and slowly added dropwise to the reaction mixture by a separatory funnel. After the completion of the dropwise addition, the temperature was raised to 60° C., and the reaction was carried out for 3 hours. Thin layer chromatography was used to track the reaction to completion, heating was stopped, and the protective device was removed. The concentrated solution was washed with water, extracted with ethyl acetate, dried and concentrated, and a crude product was obtained. The crude product was purified by silica gel column chromatography with petroleum ether:ethyl acetate=3:10 as eluent, and the eluent was concentrated under reduced pressure and dried to obtain 200.1 mg of the titled compound, a yield of 59.71%.

Example 3

Preparation of the Compound of Formula (I)

In a 250 mL three-necked flask, 241.0 mg (0.50 mmol) of silibinin and 95.8 mg (0.50 mmol) EDC were dissolved in 90 mL of tetrahydrofuran under nitrogen atmosphere. 134.0 mg (0.65 mmol) of lipoic acid was dissolved in 30 mL of tetrahydrofuran, and slowly added dropwise to the reaction mixture by a separatory funnel. After the completion of the dropwise addition, the temperature was raised to 90° C., and the reaction was carried out for 4 hours. Thin layer chromatography was used to track the reaction to completion, heating was stopped, and the protective device was removed. The concentrated solution was washed with water, extracted with ethyl acetate, dried and concentrated, and a crude product was obtained. The crude product was purified by silica gel column chromatography with petroleum ether:ethyl acetate=3:10 as eluent, and the eluent was concentrated under reduced pressure and dried to obtain 211.5 mg of the titled compound, a yield of 63.12%.

Example 4

Preparation of the Compound of Formula (I)

In a 250 mL three-necked flask, 241.0 mg (0.50 mmol) of silibinin and 95.8 mg (0.50 mmol) EDC were dissolved in 90 mL of toluene under nitrogen atmosphere. 113.3 mg (0.55 mmol) of lipoic acid was dissolved in 30 mL of toluene, and slowly added dropwise to the reaction mixture by a separatory funnel. After the completion of the dropwise addition, the temperature was raised to 65° C., and the reaction was carried out for 2 hours. Thin layer chromatography was used to track the reaction to completion, heating was stopped, and the protective device was removed. The concentrated solution was washed with water, extracted with ethyl acetate, dried and concentrated, and a crude product was obtained. The crude product was purified by silica gel column chromatography with petroleum ether:ethyl acetate=3:10 as eluent, and the eluent was concentrated under reduced pressure and dried to obtain 220.7 mg of the titled compound, a yield of 65.87%.

Example 5

Preparation of the Compound of Formula (I)

In a 250 mL three-necked flask, 241.0 mg (0.50 mmol) of silibinin and 95.8 mg (0.50 mmol) EDC were dissolved in 90 mL of acetonitrile under nitrogen atmosphere. 113.3 mg (0.55 mmol) of lipoic acid was dissolved in 30 mL of acetonitrile, and slowly added dropwise to the reaction mixture by a separatory funnel. After the completion of the dropwise addition, the temperature was raised to 60° C., and the reaction was carried out for 3 hours. Thin layer chromatography was used to track the reaction to completion, heating was stopped, and the protective device was removed. The concentrated solution was washed with water, extracted with ethyl acetate, dried and concentrated, and a crude product was obtained. The crude product was purified by silica gel column chromatography with petroleum ether:ethyl acetate=3:10 as eluent, and the eluent was concentrated under reduced pressure and dried to obtain 227.3 mg of the titled compound, a yield of 67.83%.

Example 6

Preparation of the Compound of Formula (I)

In a 250 mL three-necked flask, 241.0 mg (0.50 mmol) of silibinin and 95.8 mg (0.50 mmol) EDC were dissolved in 90 mL of tetrahydrofuran under nitrogen atmosphere. 113.3 mg (0.55 mmol) of lipoic acid was dissolved in 30 mL of tetrahydrofuran, and slowly added dropwise to the reaction mixture by a separatory funnel. After the completion of the dropwise addition, the temperature was raised to 55° C., and the reaction was carried out for 4 hours. Thin layer chromatography was used to track the reaction to completion, heating was stopped, and the protective device was removed. The concentrated solution was washed with water, extracted with ethyl acetate, dried and concentrated, and a crude product was obtained. The crude product was purified by silica gel column chromatography with petroleum ether:ethyl acetate=3:10 as eluent, and the eluent was concentrated under reduced pressure and dried to obtain 185.7 mg of the titled compound, a yield of 55.42%.

Example 7

Preparation of the Compound of Formula (I)

In a 250 mL three-necked flask, 241.0 mg (0.50 mmol) of silibinin, 113.3 mg (0.55 mmol) of lipoic acid and 12.0 mg (0.007 mmol) silicomolybdic acid were dissolved in 75 mL of 1-butyl-3-methylimidazolium tetrafluoroborate under nitrogen atmosphere. After full dissolution, the temperature was raised to 25° C. and the reaction was carried out for 8 hours. Thin layer chromatography was used to track the reaction to completion, heating was stopped, and the protective device was removed. The reaction mixture was allowed to separate into layers to give a crude product. 1-Butyl-3-methylimidazolium tetrafluoroborate was recovered and reused. The crude product was recrystallized with 90 mL methanol and dried to obtain 283.4 mg of the title compound, a yield of 84.57%.

Example 8

Preparation of the Compound of Formula (I)

In a 250 mL three-necked flask, 241.0 mg (0.50 mmol) of silibinin, 113.3 mg (0.55 mmol) of lipoic acid and 12.0 mg (0.007 mmol) silicomolybdic acid were dissolved in 75 mL of 1-butyl-3-methylimidazolium tetrafluoroborate under nitrogen atmosphere. After full dissolution, the temperature was raised to 50° C. and the reaction was carried out for 4 hours. Thin layer chromatography was used to track the reaction to completion, heating was stopped, and the protective device was removed. The reaction mixture was allowed to separate into layers to give a crude product. 1-Butyl-3-methylimidazolium tetrafluoroborate was recovered and reused. The crude product was recrystallized with 90 mL methanol and dried to obtain 265.1 mg of the title compound, a yield of 79.12%.

Example 9

Repairing Liver Injury in Animal Model with Silibinin Lipoic Acid Ester

The compound of formula (I) was prepared by the method of example 7. In order to study its protective effect on alcoholic liver injury in mice, the following animal model was designed.

Three-week-old 30-35 g SPF male mice were randomly divided into normal control group, model group, low-dose group, high-dose group and tiopronin positive control group after adaptive feeding for 3 days. The normal control group and model group were fed with basic feed every day; low dose group and high dose group were fed with basic diet every day and were given the compound of formula (I) of 10 mg/kg/day and 50 mg/kg/day, respectively; tiopronin positive control group was fed with basic feed and 50 mg/kg/day tiopronin. Ethanol 3 g/kg/day (0.01 mL/g) was given to the model group, low dose group, high dose group and tiopronin positive control group. The normal control group was given distilled water of the same volume. After 25 days, fasting for 2 hours after the last administration, glutamic pyruvic transaminase (ALT), glutamic oxaloacetic transaminase (AST) and triglyceride (TG) were measured in serum by decapitation.

TABLE 1

Effects of Compound of Formula (I) on Serum TG, ALT and AST in Mice with Alcoholic Liver Injury

| Group | ALT (U/L) | AST (U/L) | TG (mmol/L) |
|---|---|---|---|
| Normal control group | 55.87 ± 9.42 | 130.50 ± 17.22 | 0.899 ± 0.32 |
| Model group | 80.52 ± 13.39 | 178.62 ± 10.86 | 1.985 ± 0.42 |

TABLE 1-continued

Effects of Compound of Formula (I) on Serum TG, ALT and AST in Mice with Alcoholic Liver Injury

| Group | ALT (U/L) | AST (U/L) | TG (mmol/L) |
|---|---|---|---|
| Tiopronin positive group | 65.32 ± 8.79 | 141.37 ± 18.75 | 1.156 ± 0.33 |
| High dose group | 57.21 ± 2.93 | 134.56 ± 6.57 | 0.873 ± 0.35 |
| Low dose group | 61.72 ± 10.37 | 139.84 ± 18.95 | 0.902 ± 0.19 |

Example 10

The Antioxidant Activity of the Silibinin Lipoic Acid Ester Measured by a DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in toluene to prepare a 0.2 mmol/L DPPH solution, stored at 0° C. in dark.

Preparation of test solution: Vc (vitamin C, positive control), compound of formula (I) (sample), silibinin (control) and lipoic acid (control). The sample solution was subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 2).

TABLE 2

Dilution Gradient of the Test Solutions

| Number | Test solution | Concentration gradient/ppm |
|---|---|---|
| Vc | Vc | 1.76, 8.80, 21.12, 42.24, 79.20, 112.64, 281.60, 492.80, 792.00, 915.20 |
| A | Compound of Formula (I) | 1.76, 8.80, 21.12, 42.24, 79.20, 112.64, 281.60, 492.80, 792.00, 915.20 |
| B | Silibinin | 1.76, 8.80, 21.12, 42.24, 79.20, 112.64, 281.60, 492.80, 792.00, 915.20 |
| C | Lipoic acid | 1.76, 8.80, 21.12, 42.24, 79.20, 112.64, 281.60, 492.80, 792.00, 915.20 |

Specific Steps:

Sample liquid absorbance measurement: Take 2 mL of sample solution (Table 2 Vc, B, C), add 2 mL of DPPH solution with concentration of $2 \times 10^{-4}$ mol/L, mix and react in the dark at room temperature for 30 min, adjust to zero with toluene, and measure at 517 nm. The absorbance Ai was simultaneously measured for the absorbance Aj of 2 mL of toluene mixed with 2 mL of the sample solution and the absorbance Ao of 2 mL of DPPH solution mixed with 2 mL of toluene (the experimental results are shown in Table 3).

TABLE 3

Absorbance Test Results of Each Test Solution

| Sample | Absorbance | \multicolumn{10}{c}{Concentration/ppm} |
|---|---|---|---|---|---|---|---|---|---|---|---|
| | | 1.76 | 8.80 | 21.12 | 42.24 | 79.20 | 112.64 | 281.60 | 492.80 | 792.00 | 915.20 |
| Vc | Ai | 0.718 | 0.624 | 0.222 | 0.142 | 0.091 | 0.078 | 0.076 | 0.070 | 0.074 | 0.065 |
| | Aj | 0.068 | 0.061 | 0.090 | 0.054 | 0.069 | 0.057 | 0.062 | 0.062 | 0.066 | 0.059 |
| | Ao | | | | | | 0.846 | | | | |
| A | Ai | 0.736 | 0.682 | 0.598 | 0.509 | 0.300 | 0.226 | 0.203 | 0.155 | 0.134 | 0.099 |
| | Aj | 0.039 | 0.045 | 0.059 | 0.061 | 0.057 | 0.059 | 0.054 | 0.049 | 0.055 | 0.048 |
| | Ao | | | | | | 0.795 | | | | |
| B | Ai | 0.897 | 0.887 | 0.767 | 0.714 | 0.616 | 0.553 | 0.410 | 0.366 | 0.315 | 0.290 |
| | Aj | 0.052 | 0.049 | 0.051 | 0.042 | 0.058 | 0.054 | 0.043 | 0.051 | 0.037 | 0.039 |
| | Ao | | | | | | 0.923 | | | | |
| C | Ai | 0.883 | 0.969 | 0.797 | 0.730 | 0.626 | 0.579 | 0.453 | 0.330 | 0.291 | 0.267 |
| | Aj | 0.053 | 0.045 | 0.048 | 0.045 | 0.057 | 0.056 | 0.043 | 0.042 | 0.040 | 0.031 |
| | Ao | | | | | | 0.896 | | | | |

Clearance calculation: clearance rate (%)=[1−(Ai−Aj)/Ao]*100%

TABLE 4

DPPH Clearance Rate Experiment Results

| | \multicolumn{3}{c}{Clearance rate/% ( n = 3)} | | |
|---|---|---|---|---|
| Concentration/ppm | Vc | A | B | C |
| 1.76 | 23.16 | 12.28 | 8.42 | 7.27 |
| 8.80 | 33.47 | 19.80 | 9.16 | 8.52 |
| 21.12 | 79.63 | 32.16 | 22.43 | 16.42 |
| 42.24 | 89.55 | 43.55 | 27.10 | 23.54 |
| 79.20 | 97.42 | 69.42 | 39.53 | 36.45 |
| 112.64 | 97.53 | 78.95 | 45.87 | 41.58 |
| 281.60 | 98.29 | 81.21 | 60.25 | 54.23 |
| 492.80 | 99.06 | 86.70 | 65.88 | 67.82 |
| 792.00 | 99.10 | 90.06 | 69.85 | 72.01 |
| 915.20 | 99.28 | 93.52 | 72.76 | 73.69 |

According to the experimental results of FIG. 1 and Table 2-4, the antioxidant activity of compound formula (I) (A) showed a concentration-dependent relationship, and the scavenging ability of compound formula (I) (A) to DPPH radical increased with the increase of concentration. In the determined concentration range, the highest scavenging rate of DPPH radical was 93.52%. At the same time, compared with the positive control Vc group, the scavenging ability of compound formula (I) (A) was slightly weaker. Compared with the control group treated with silibinin (B) and lipoic acid (C) alone, the scavenging ability of compound formula (I) (A) to scavenge DPPH free radicals was better at the same concentration. The antioxidant activity at higher concentration was much higher than that of silibinin (B) control group and lipoic acid (C) control group.

The above experimental results prove that the compound has excellent liver protective activity and antioxidant activity, and can be used as a new type of liver protection product in health products and drugs.

What is claimed is:

1. A compound having the following formula (I):

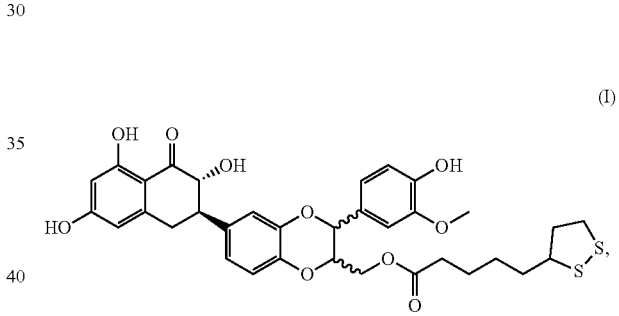

(I)

wherein the compound is a mixture of two diastereomers and has a protective effect on alcoholic liver injury in mice and a concentration-dependent antioxidant activity.

2. A method of preparing the compound of claim 1, comprising:
reacting a compound of formula (II) with a compound of formula (III) to obtain the compound of formula (I):

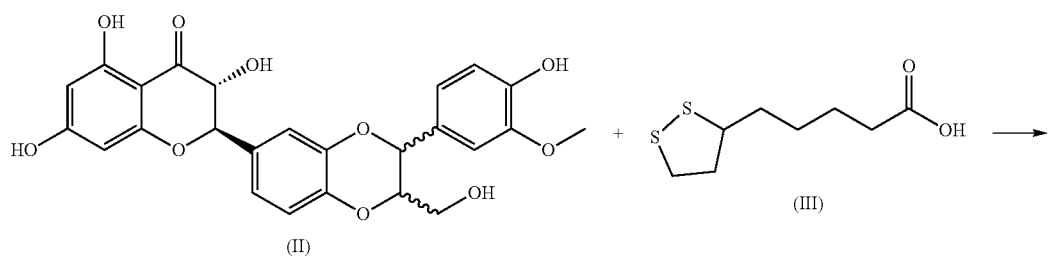

-continued

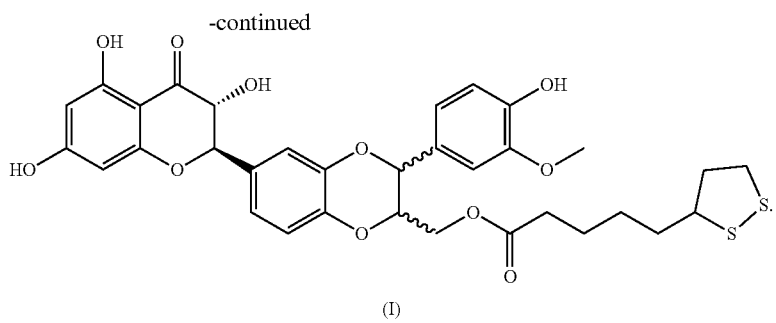

(I)

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalyst under nitrogen atmosphere to obtain a reaction mixture;
heating the reaction mixture at 50-85° C. for 1-4 hours;
concentrating the reaction mixture under reduced pressured to give a crude product; and
purifying the crude product on a silica gel column with petroleum ether and ethyl acetate as an eluent to obtain the compound of formula (I).

4. The method of claim 3, wherein the organic solvent is toluene, ethyl acetate, or acetonitrile.

5. The method of claim 3, wherein the catalyst is EDC.

6. The method of claim 3, wherein the molar ratio of the compound of formula (II) and the compound of formula (III) is 1:1.1.

7. The method of claim 3, wherein the reaction mixture is heated at 75° C.

8. The method of claim 3, wherein the reaction mixture is heated for 4 hours.

9. The method of claim 3, wherein the eluent is ethyl acetate:petroleum ether=3:10.

10. The method of claim 2, wherein the reaction of the compound of formula (II) with the compound of formula (III) comprises the following steps:

placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 25-50° C. for 5-10 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-butyl-3-methylimidazolium tetrafluoroborate ([BMIM][$BF_4$]).

12. The method of claim 10, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 10, wherein the reaction mixture is heated at 25° C.

15. The method of claim 10, wherein the reaction mixture is heated for 8 hours.

* * * * *